United States Patent [19]
Burkhardt, Jr.

[11] Patent Number: 4,586,379
[45] Date of Patent: May 6, 1986

[54] ULTRASONIC PIPE INSPECTION SYSTEM

[75] Inventor: Frederick R. Burkhardt, Jr., Chester, Va.

[73] Assignee: Virginia Corporation of Richmond, Chester, Va.

[21] Appl. No.: 655,903

[22] Filed: Sep. 28, 1984

[51] Int. Cl.⁴ .............................................. G01N 29/04
[52] U.S. Cl. ...................................... 73/622; 73/637; 73/638
[58] Field of Search ................... 73/622, 637, 638, 640

[56] References Cited
U.S. PATENT DOCUMENTS

| | | | |
|---|---|---|---|
| 4,279,158 | 7/1981 | Kajiyama et al. | 73/637 |
| 4,331,034 | 5/1982 | Takeda et al. | 73/637 |
| 4,383,448 | 5/1983 | Fujimoto et al. | 73/637 |
| 4,387,598 | 6/1983 | Jamieson | 73/622 |
| 4,389,894 | 6/1983 | Kajiyama | 73/637 |
| 4,474,064 | 10/1984 | Naruse et al. | 73/622 |
| 4,515,018 | 5/1985 | Kajiyama | 73/637 |

Primary Examiner—Howard A. Birmiel
Attorney, Agent, or Firm—John F. C. Glenn

[57] ABSTRACT

Remote-controlled system for moving an ultrasonic transducer assembly around a pipe where it has a welded joint between a straight pipe section and a curved or straight pipe section. The system includes a platform movable along an arm projecting from a carriage on a track around the pipe, and a pressure cylinder and universal joint connecting the platform to the transducer assembly. Couplant fluid is fed continuously to the surface of the assembly engaging the pipe as it slides over the pipe.

12 Claims, 15 Drawing Figures

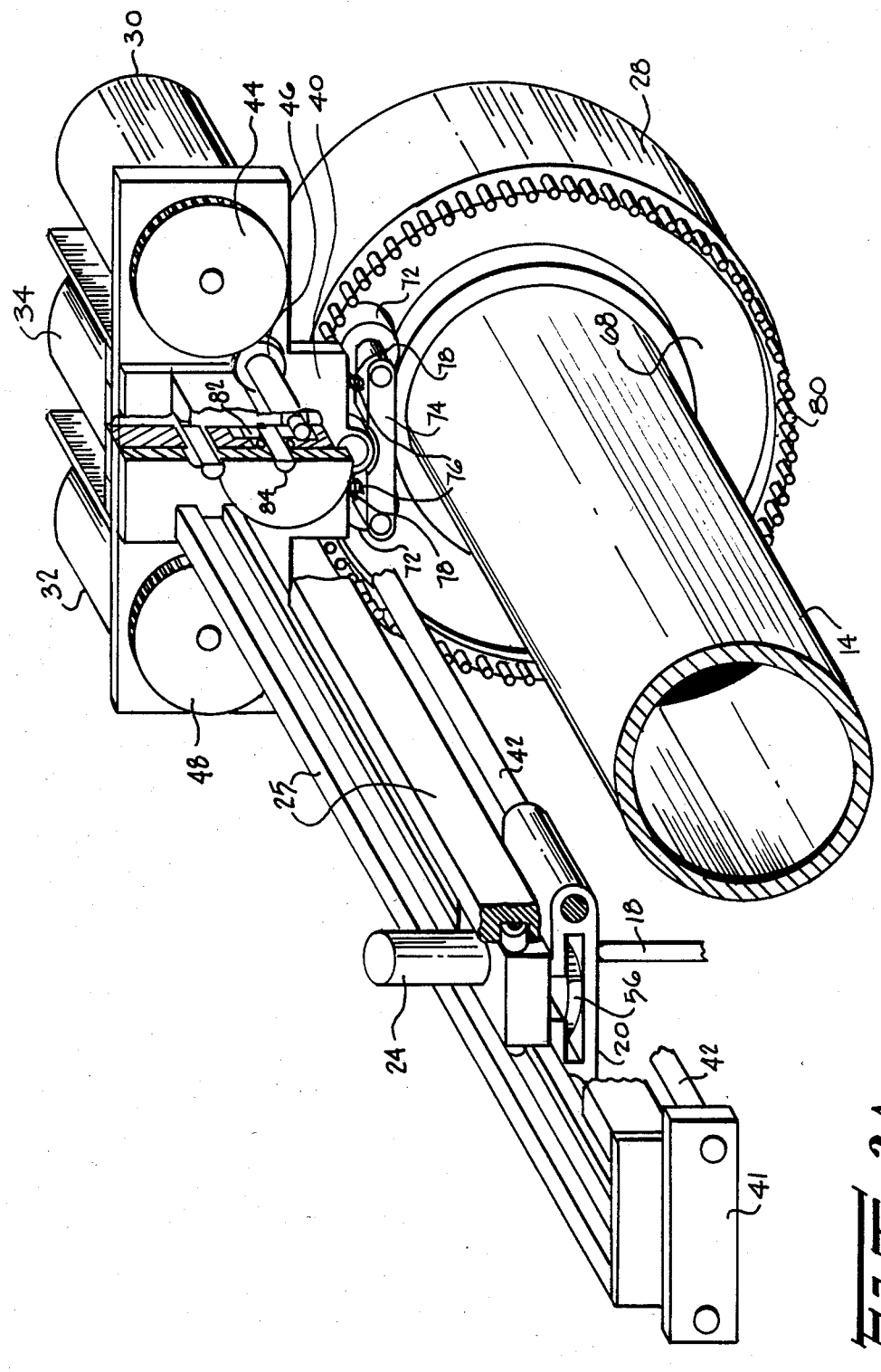

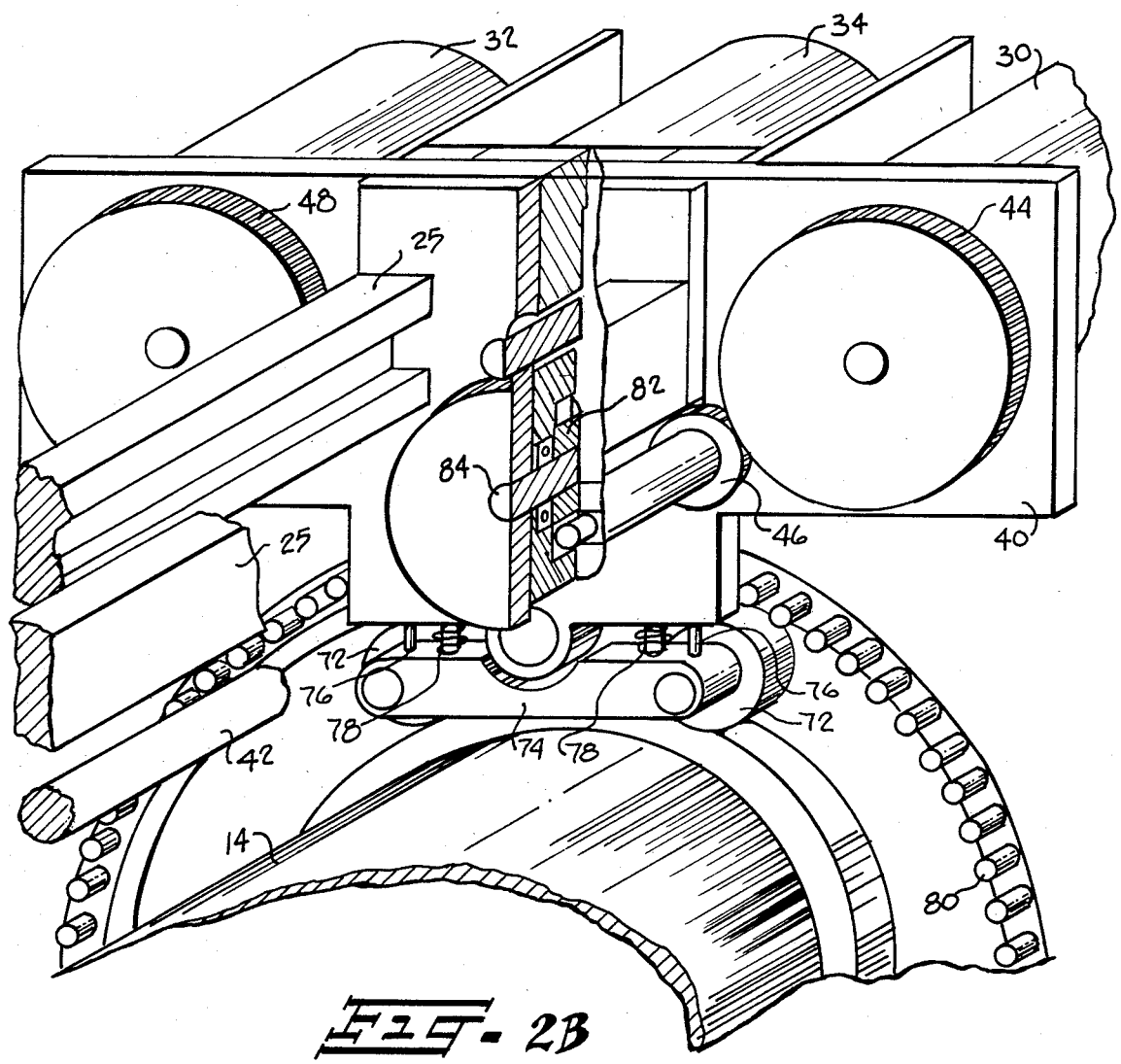
FIG-2B
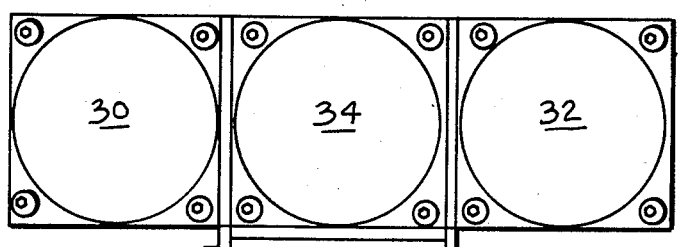
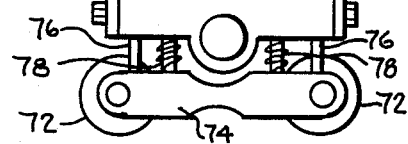
FIG-6

Fig-3

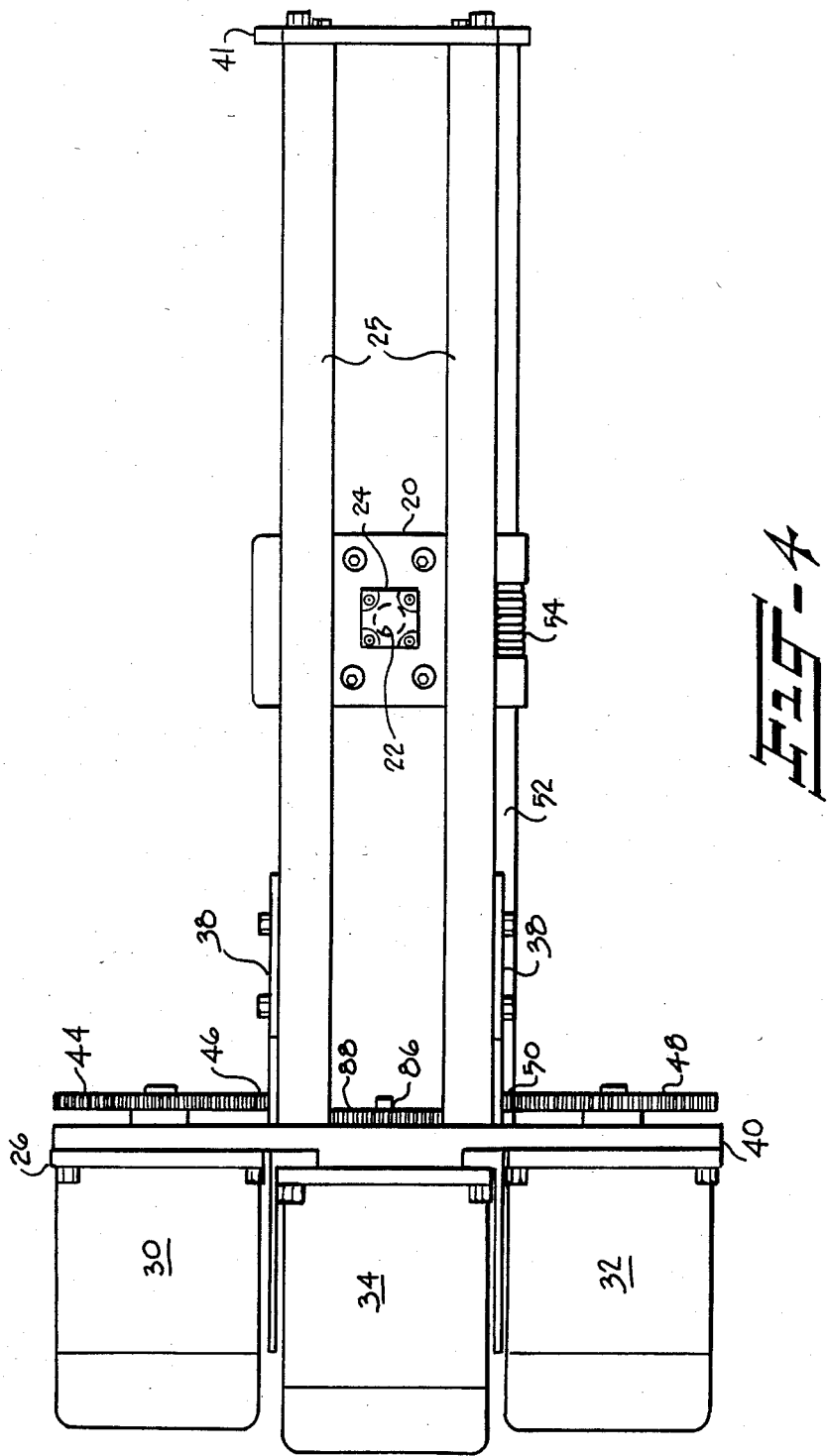

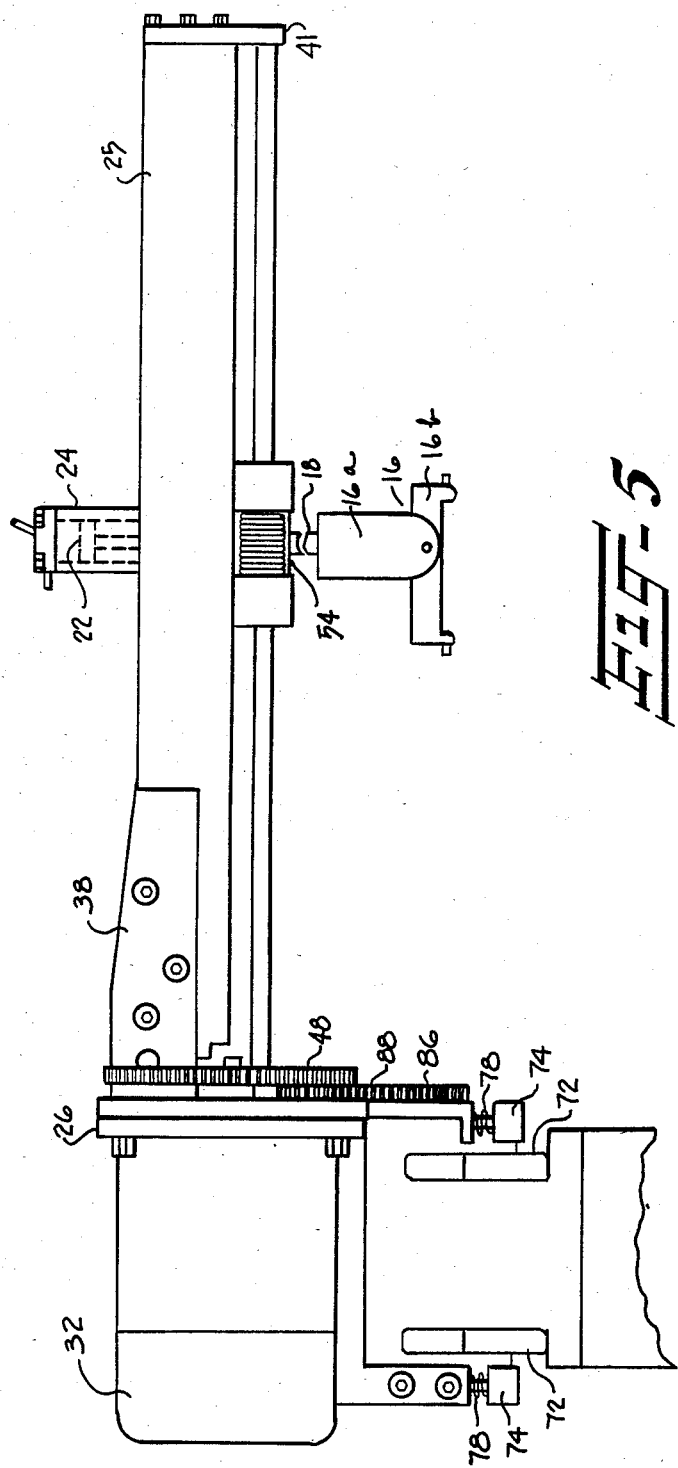

ULTRASONIC PIPE INSPECTION SYSTEM

BACKGROUND OF THE INVENTION

Pipe welds require periodic reinspection in critical applications, such as in nuclear power stations, and remote control is often required for inspection in order to minimize risk to the operating personnel. The inspecting instrument is usually an ultrasonic transducer moving around and in conductive contact with the pipe adjacent the weld area. The design of remote controlled equipment for carrying this instrument around bends in the piping has presented difficulties and various designs have been proposed, as, for example, in U.S. Pat. No. 4,383,448 and European Patent Application Nos. 0065262 published Nov. 24, 1982, and 0081214 published June 15, 1983. However, there has been a continuing need for an improved design for this purpose, combining improved operation capability with simplified construction.

The use of couplant fluid for ultrasonic transmission between transducer and pipe has also presented difficulties in this application. If the fluid is not replenished during use the performance of the transducer will suffer, but replenishment is complicated by the necessary movement of the transducer around the pipe weld. An approach has been made to solving this problem by using a couplant-filled membrane bag that conforms to changing contours and retains all of the couplant. However, this requires changes in the transducer assembly that increase costs, so a need has remained for a better solution.

SUMMARY OF THE INVENTION

In accordance with the present invention, an ultrasonic transducer assembly is mounted on a universal joint to enable its pipe-contacting surface to lie closely against a pipe while the universal joint is maneuvered to cause the assembly to move circumferentially around the pipe, while pressing the assembly against the pipe and moving it along the weld around the pipe, while controlling the angle of the transducer relative to its direction of movement, and while replenishing couplant fluid between the pipe and the pipe-contacting surface of the assembly. The means for achieving these movements will become apparent as the following description of a present preferred embodiment of the invention proceeds.

BRIEF DESCRIPTION OF THE DRAWINGS

The accompanying drawings illustrate the present preferred embodiment of the invention, as follows:

FIGS. 2A & B show a schematic isometric view, partially broken away and sectioned, of apparatus of the kind shown in FIG. 1 and including a portion of a pipe (in reduced scale) having a circular track (in exaggerated scale) mounted around it, and part of the apparatus movable around the track for carrying an ultrasonic transducer assembly (not shown), viewed from above the carrying apparatus and pipe when the carrying apparatus is positioned above the pipe and track;

Figure 3:
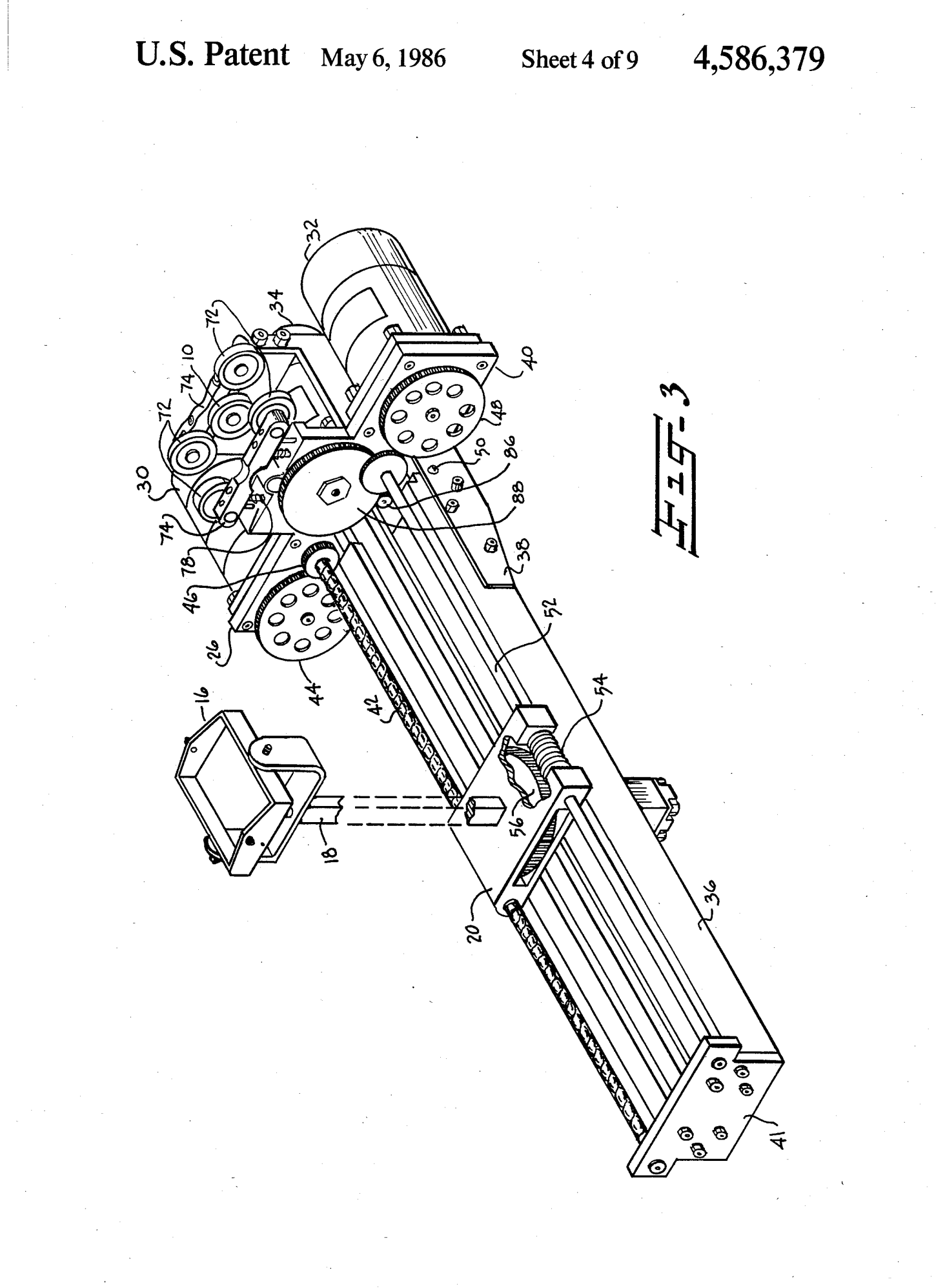

FIG. 3 is a view of the carrying apparatus shown in FIG. 2, but omitting the pipe and track, viewed from above the carrying apparatus after it is inverted from its FIG. 2 position;

FIG. 4 is a top plan view of the carrying apparatus shown in FIGS. 2 and 3, as seen from above the apparatus when it is positioned as in FIG. 1 above the pipe and track (not shown);

FIG. 5 is a side view of what is shown in FIG. 4;

FIG. 6 is an end view of what is shown in FIG. 5, viewed from the left of FIG. 5;

DETAILED DESCRIPTION OF THE PRESENT PREFERRED EMBODIMENT

Figure 1:
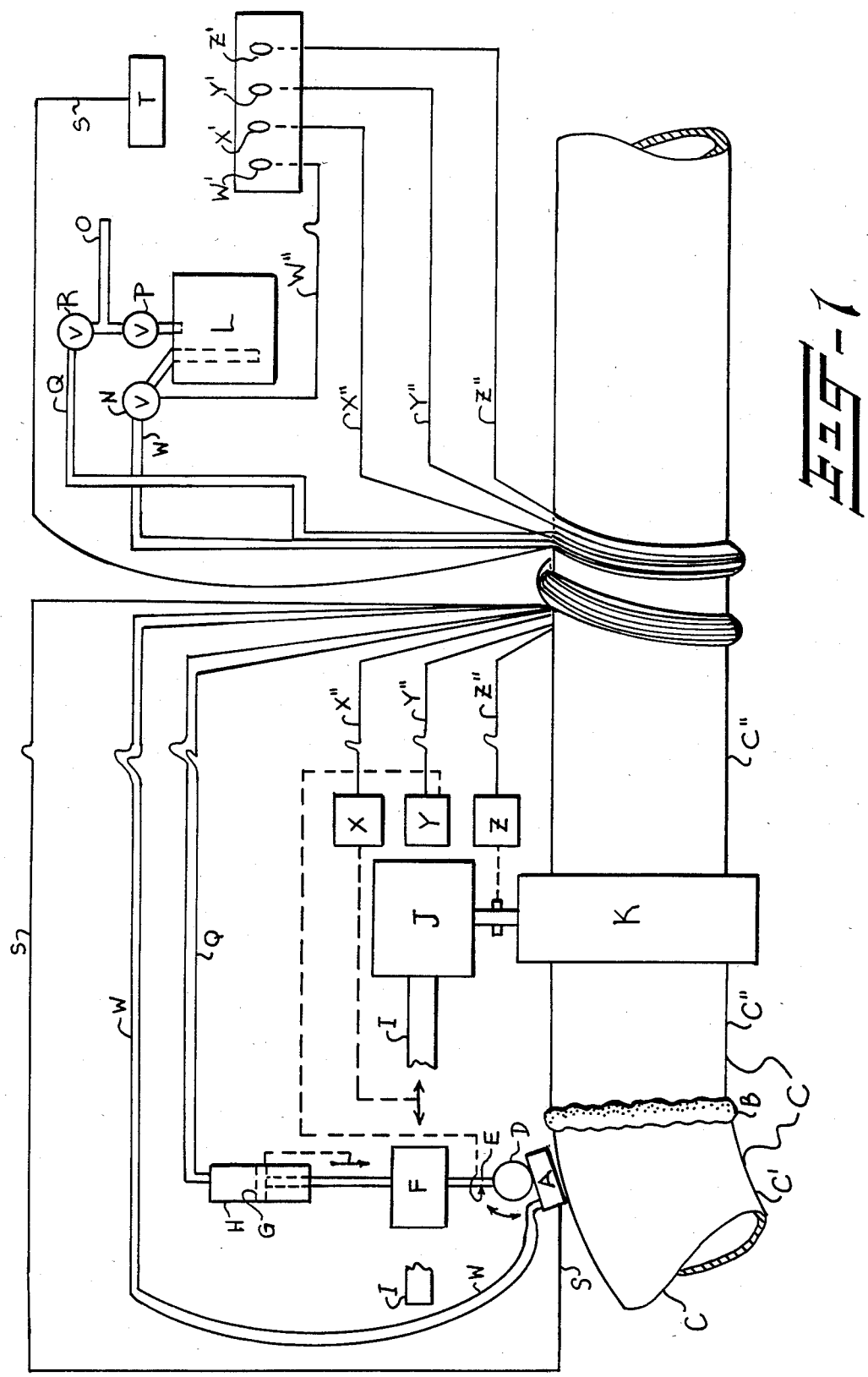
FIG. 1 diagramatically illustrates the principal components of the present preferred embodiment of the invention.
Figure 7:
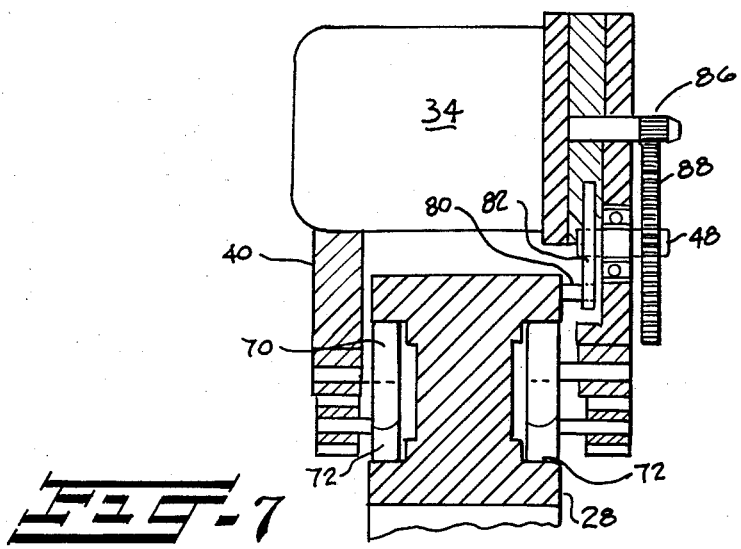
FIG. 7 shows a partially broken away view of a section through the carrying apparatus and track, taken on a plane passing through the axis of rotation of the motor and through the axis of curvature of the track.
Figure 8:
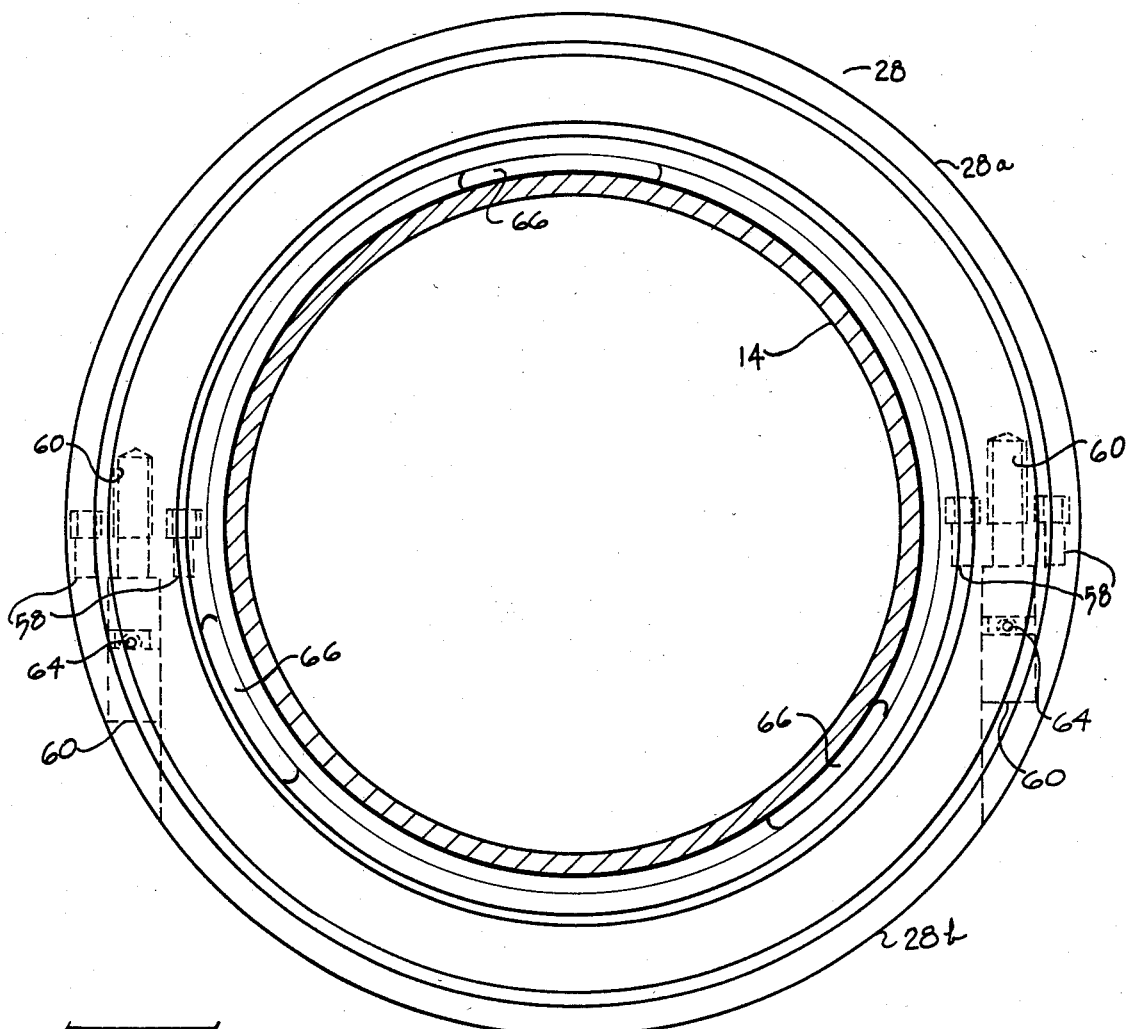
FIG. 8 shows a section of the pipe taken normal to its axis and the adjacent unsectioned track mounted on the pipe, in corrected scale, as viewed from beyond the right end of FIG. 2.
Figure 9:
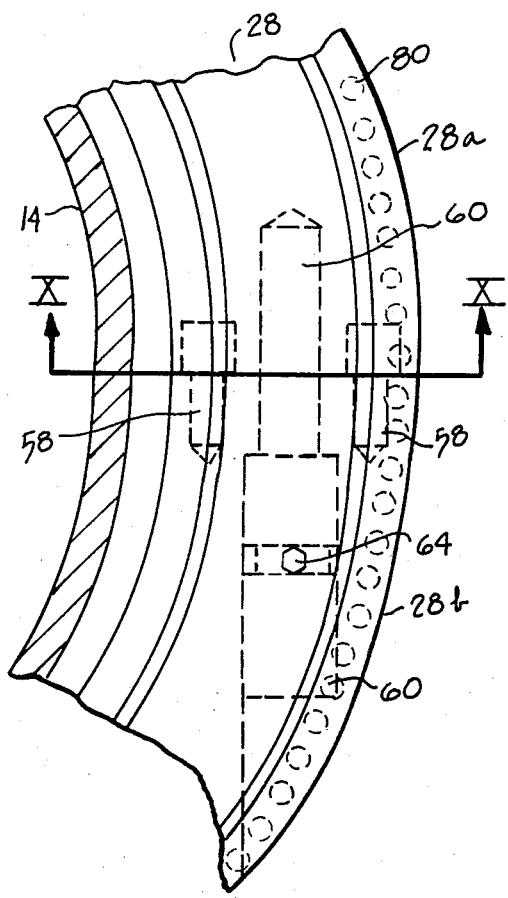
FIG. 9 shows an enlarged and broken away view of the left side of FIG. 8.
Figure 10:
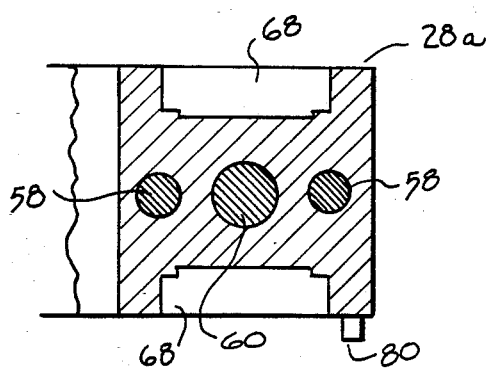
FIG. 10 shows a section on the lines in FIG. 8.
Figure 11:
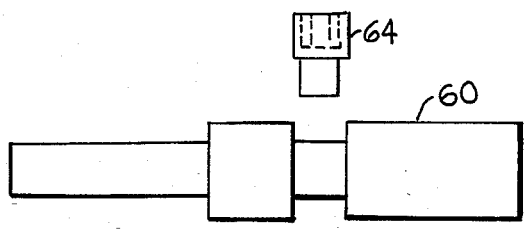
FIG. 11 shows one of the pins which holds the ends of the two sections of the track together, with the associated set screw in adjacent exploded relation.
Figure 12:
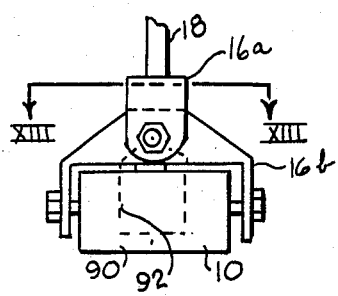
FIG. 12 shows an end view of the universal joint and an ultrasonic transducer assembly therein, as oriented when the carrying apparatus is positioned above the pipe and tracks.
Figure 13:
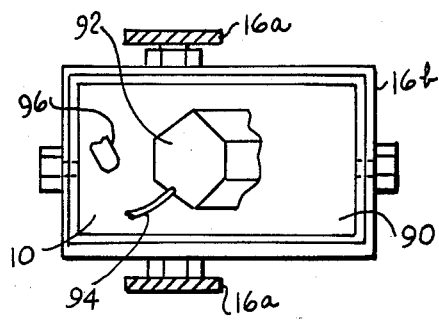
FIG. 13 shows a section on the line XIII—XIII in FIG. 12.
Figure 14:
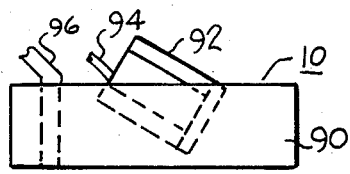
FIG. 14 shows a side view of the transducer assembly shown in FIG. 13 after removal of the universal joint.

Referring now to the accompanying drawings, and initially to the diagramatic illustration of the invention in FIG. 1, an ultrasonic transducer assembly A is shown adjacent a weld B around a bend in a pipe C, where an elbow C' is welded to a straight section C''. The assembly A is connected by a universal joint D to one end of a shaft E extending slidably through a platform F. The other end of shaft E is secured to a piston G in a cylinder H. This cylinder is mounted on platform F, which in turn is carried by an arm I (shown broken away) extending from a carriage J. A track K is removably fastened around straight pipe C'' to support and guide carriage J around the pipe.

A flexible hose W supplies a flow of ultrasonically conductive composition, which is a conventional fluid known as "couplant", to the pipe-contacting surface of transducer assembly A. Hose W receives this flow from a couplant supply tank L. Couplant flow is controlled by air pressure in tank L supplied by a hose O from an external compressed air source (not shown) through an adjustable pressure regulator P. The couplant flow from tank L through hose W is started and stopped by a solenoid valve N operated by a remote control W'.

Pressure hose O also supplies air through a hose Q connected to cylinder H to actuate piston G. An adjustable pressure regulator R is connected to hose Q to regulate the amount of air pressure on piston G. This adjustment is made manually before a test run, in the area where the test pipe is located, since experience has shown that remote control of the cylinder H pressure is unnecessary in the course of a run.

Motors X, Y and Z are mounted on carriage J, with connections from the motor X to move platform F toward and from carriage J, from motor Y to rotate shaft E, and from motor Z to move carriage J around track K. Remote controls W', X', Y', and Z' are connected through cables W''', X''', Y''' and Z''' to solenoid valve N and motors X, Y and Z, respectively, to control their movement. In this way, movement of transducer assembly A relative to weld B is controlled, as follows:

(1) Motor X causes transducer assembly A to move across, toward or from weld B, by causing platform F to move toward and from carriage J, carrying with it cylinder H, shaft E and transducer assembly A.

(2) Motor Y causes shaft E to rotate transducer assembly A and thus control the angle at which its ultrasonic waves are directed toward weld B, to achieve a desired direction of the waves or to swing across a desired range of directions of the waves.

(3) Motor Z causes transducer assembly A to move around pipe C and weld B by causing carriage J to travel around track K, carrying with it motors X, Y and Z, arm I, platform F, cylinder H, piston G, shaft E, universal joint D and transducer assembly A, while tank L, valves N, P and R, and remote controls W', Y', Z' and T remain at their fixed locations.

(4) Piston G and cylinder H move transducer assembly A against pipe C and holds it there while inspection is taking place, which may be while none or any one or more of the above motions are taking place.

(5) While any one or more of the said motions are occurring under control of motors X, Y and Z and solenoid valve N, the universal joint D automatically accomodates the angle of transducer assembly A relative to the central axis of shaft E so that the flat contacting bottom surface of transducer assembly A will tilted to be be as close as possible against the opposite pipe surface, for optimum contact for wave transmission through the couplant conventionally used between said surfaces. Universal joint D may be of a conventional two-piece kind capable of transmitting pressure and rotational forces while changing its angle of transmission in any direction, or it may simply be a flexible shaft having these functions.

An electrical cable S connects transducer assembly A to an ultrasonic test instrument T capable of initiating and sensing signals to and from transducer assembly A as it probes a weld, and displaying the results. This cable S and cables W''', X''', Y''' and Z''', together with hoses W and Q, have enough flexibility and extra length to enable them to extend loosely around pipe C while carriage J carries transducer assembly A, cylinder H and motors X, Y and Z at least a full revolution around pipe C, and preferably at least two revolutions. As shown in FIG. 1, this wrap-around preferably occurs on the opposite side of track K from the position of weld B. Thus, these cables and hoses permit transducer assembly A to be moved by remote control Z' all the way around one side of weld B, and then, after being moved by remote control X' over to the other side of weld B and redirected by remote control Y', to be moved by remote control Z' around pipe C once more in the same direction, to probe the said other side of weld B. Such inspection of the other side of the weld could be done by reversing the direction of carriage J, but this is not presently preferred.

This arrangement provides great flexibility in using remote controlled weld scanning equipment where pipe bends and the like are welded to straight sections in plants requiring such equipment, as well as being useful where a pair of straight sections are welded together.

Details of the present preferred embodimemt of such equipment are illustrated in the remaining FIGS. 2–14, where the elements which correspond to those in FIG. 1 are identified as follows:

10—Transducer assembly A
12—Weld B
14—Pipe C
16—Universal joint D
18—Shaft E
20—Platform F
22—Piston G
24—Cylinder H
25—Arm I
26—Carriage J
28—Track K
30—Motor X
32—Motor Y
34—Motor Z
94—Hose S
96—Hose W Platform 20 slides on a pair of parallel projecting arms 25 secured at one end by brackets 38 to base plate 40 of carriage 26. A spirally threaded shaft 42 extends through a correspondingly threaded opening through platform 20, in order to move platform 20 along arms 36 when shaft 42 is rotated by motor 30 through a gear 44 fixed on the drive shaft of motor 30, and a pinion 46 fixed on shaft 42. One end of shaft 42 is journaled in base plate 40 of carriage 26, and the other end in a plate 41 across the projecting ends of arms 25.

Motor 32 drives a gear 48 driving a pinion 50 fixed on a shaft 52 carrying a worm 54. Shaft 52 is slidable endwise through the worm 54 but has a square or other non-circular cross-section fitting in a correspondingly shaped opening through worm 54, so that they must rotate together. The ends of shaft 52 are journaled in plates 40 and 41. Worm 54 drives a gear 56 journaled in platform 20. A square or other non-circular opening extends through the center of gear 56 for receiving shaft 18, which has a correspondingly shaped cross-section. Shaft 18 is slidable lenthwise relative to gear 56, but rotates with gear 56. When motor 30 operates to move platform 20 along arms 36, worm 54 slides along shaft 52 and does not rotate unless it is driven by motor 32 through shaft 52. Thus, the movements of shaft 18 endwise under control of cylinder 24, rotationally under control of motor 32, and laterally along arms 36 under control of motor 30, are each controllable independently of the others, and each movement can occur alone or simultaneously with one or more of the others. The same is true of movement of shaft 18 with carriage 26 around pipe 14 under control of motor 34, as will now be described.

Track 28 for carriage 26 is in the form of two semicircular rails 28a and 28b placed around pipe 14 and fastened together at their ends. A pair of alignment pins 58 project from the opposite ends of rail 28a into aligning sockets formed in the opposite ends of rail 28b, and a pair of threaded studs 60 are housed in the ends of rail 28b and screwed into aligned female threads in the opposite ends of rail 28a. Each of the studs 60 has a circumferential groove 62 for receiving the end of a set screw 64 inserted through the side of rail 28b perpendicular to the axis of the pin 60. These set screws are inserted into rails 28b far enough to control the axial position of studs 60 while not interfering with their rotary movement. This prevents studs 60 from sliding axially until they fall out of the rails during assembly, and enables them to be rotated to force apart the joint between the rails during disassembly, against the frictional resistance of aligning pins 58 coming out of their close-fitting aligning sockets. Before mounting and fastening the rails around pipe C, carriage 26 must be mounted on one of the rails, and at least three equally spaced rubberlike pads 66 are placed between the rails and pipe so that they will be in tightly maintained radial alignment when the studs 60 have been screwed tightly in place.

The cross section of each of the rails 28a and b is generally H-shaped, with the sides of the H extending parallel to the central axis of track 28. A pair of grooves 68 thus extends around opposite sides of rails 28a and b. Each groove 68 receives a wheel 70 which rolls around the outer circumference of one of the grooves 68, and also receives a pair of wheels 72 journaled in a yoke 74 slidable along studs 76 projecting from the frame of carriage 26 toward the said inner circumference of groove 68. Compression springs 78 around studs 76 press yoke 74 and thus wheels 72 against the said groove inner circumference, and the corresponding opposite pressure of spring 78 on the frame of carriage 26 causes wheel 75 to press against the opposite groove outer circumference. Deflection of carriage arms 36 toward or from pipe 14 is resisted by springs 78 on one side or the other of track 28, and the springs 78 are selected for sufficient stiffness to prevent significant deflection under normal operating conditions. While not essential, it may be convenient to add a screw (not shown) next to and paralleling each of the studs 76, with the threaded end of the screw secured in the frame above yoke 74 as seen in FIGS. 2A & B, with an unthreaded portion of the screw passing slidably through an opening through yoke 74, and with the head of the screw engageable with yoke 74 to prevent excessive movement under the pressure of springs 78 during assembly.

In order to provide a positive indexed movement of carriage 26 and transducer assembly 10 around pipe 14, equally spaced pins 80 are mounted around the side of track 28 adjacent its outer periphery. These pins project parallel to the axis of track 28, and mesh with a sprocket wheel 82 on the same shaft 84 as a gear 88 driven by a pinion 86 on the drive shaft of motor 34. Thus, motor 34 drives sprocket wheel 82 to rotate carriage 26 relative to pins 84 and track 28. As will be understood by those familiar with such controls, motor 34 is preferably of the stepping type and is used with digital controls to provide a record of the position of carriage 16 around track 28 when each probe of transducer assembly 10 is recorded. For example, motor 34 may be provided with an encoder which delivers two signals every 1.8° of motor rotation, and these signals may be processed as counts in either a clockwise or counter clockwise direction. This information may be processed to determine location of carriage 26 and assembly 10 relative to a marked position on the pipe. The other positional aspects of transducer assembly 10 are recorded at the same time, through a conventional computer readout system.

As shown in FIGS. 3 and 12-14, the universal joint 16 has a pair of brackets 16a and 16b hinged to each other. The outer bracket 16a is fixed on the end of shaft 18 and the inner bracket 16b is hinged to a conventional plastic block 90 carrying a conventional ultrasonic transducer 92 (forming assembly 10 corresponding to assembly A shown in FIG. 1). A cable 94 (corresponding to cable S shown in FIG. 1) carries power and signal lines to transducer 92. A hose 96 (corresponding to hose W in FIG. 1) carries couplant composition to a passage 97 through block 90 and its lower surface 98 which is adapted to bear against pipe 14. Transducer 92 transmits and receives at an angle through surface 98, as indicated by its angle to the surface shown in FIGS. 13 and 14.

While a present preferred embodiment of the apparatus and practice of the invention has been illustrated and described, it will be understood that it may be otherwise variously embodied and practiced within the scope of the following claims.

I claim:

1. Apparatus for moving an ultrasonic transducer around a welded joint between two end-to-end portions of a pipe, comprising:
   (i) means having a surface slidable against a pipe wall and adapted to mount an ultrasonic transducer capable of transmitting and sensing at an angle through said surface for weld inspection;
   (ii) supporting means, and means connecting said supporting means to said mounting means so that said surface is tiltable to follow the contour of a pipe while pressure is transmitted through the connecting means to said surface;
   (iii) the connecting means being rotatable to cause rotation of said surface about itself while against a pipe and thereby change the direction of transmission to a transducer in the mounting means, such rotation being substantially independent of any sidewise movement of the surface;
   (iv) means to cause the connecting means to press said surface against a pipe;
   (v) means to slide said surface around and between both sides of a weld around a pipe, comprising an arcuate track mountable around a pipe, a carriage movable around the track, and an arm extending from the carriage generally parallel to the central axis through the track and secured to the carriage against endwise movement relative to the carriage, said supporting means being movable along the arm and carrying with it said connecting means and mounting means for movement toward and from the carriage when the supporting means moves along the arm, and for swinging movement around a pipe on which the track is mounted when the carriage moves around the track; and
   (vi) drive transmission means connected to the connection means to rotate the slidable surface, comprising a component mounted on and carried by the carriage, another component mounted on and carried by said supporting means for movement toward and from the carriage and the first-mentioned component, and means extending between and connecting said components for transmission of rotary drive from the first mentioned component to the other component while permitting said movement toward and from each other.

2. Apparatus according to claim 1, in which the pressure causing means is a piston and cylinder in the connecting means between said support and the portion of the connecting means which permits said surface to tilt.

3. Apparatus according to claim 1, comprising independently operable motors mounted on the carriage, one of said motors being connected to drive the carriage around the track, a second one of said motors being connected to move the support along the arm, and a third one of said motors being connected to drive the rotatable means which is carried by the carriage.

4. Apparatus according to claim 3, comprising control means mountable in remote fixed positions for each of said motors, and flexible cables connecting said motors to said control means, said cables being long enough to wrap around a pipe on which the track is mounted as the carriage moves around the track at least once while the controls means are stationary, 5. Apparatus according to claim 1, wherein the track is of substantially H-shaped cross section, with the sides of the H extending parallel to the central axis around which the track means is curved, wherein the means supporting the carriage on the track comprises wheels rolling in the groove resulting from said cross section, each side of the groove having a wheel rolling against it, and wherein compression springs operating on said wheels oppose deflection of said arm.

6. Apparatus according to claim 1, comprising means to transmit ultrasonic tranducer couplant fluid to said surface as it slides against a pipe during movement of the carriage around the track.

7. Apparatus according to claim 6, comprising means to supply couplant fluid from a fixed position, means carried with the transducer mounting means for transmitting couplant fluid to said surface, and a flexible tube connecting said supply means and transmitting means to replenish the supply of couplant fluid in the transmitting means, said tube being long enough to wrap around a pipe on which said track is mounted as the carriage moves at least once around the track.

8. Apparatus according to claim 7, in which the tube is long enough to permit the carriage to move at least twice around the track.

9. Apparatus according to claim 2, comprising means to supply air under pressure to said cylinder from a fixed position, and a flexible tube connecting said supply means to the cylinder, said tube being long enough to wrap around a pipe on which the track is mounted as the carriage moves at least once around the track while the supply means remains stationary.

10. Apparatus according to claim 1, in which said track comprises a plurality of separate arcuate segments aligned end to end, each pair of adjacent ends having projections from one extending into close-fitting openings in the other for alignment, having an elongated member extending rotatably through an opening in either of said ends into a threaded opening in the other of said ends, and having means to restrain said member against endwise movement through said opening while permitting rotational movement, said member being threaded where it extends into said threaded opening, whereby the member may be rotated to pull together said ends and counter-rotated to force them apart against the frictional resistance of the aligning projections in their close-fitting openings.

11. Apparatus according to claim 3, comprising uniformly spaced parallel pins projecting outwardly from one side of the track parallel to and equidistant from the axis of curvature of the track, and a gear driven by the said first one of said motors and meshing with said pins.

12. Apparatus according to claim 1, wherein the drive transmission means component carried on the supporting means comprises a gear rotatable with said connecting means and a helical worm meshing with said gear and rotatable by and slidable along the connecting means between the transmission components.

* * * * *